United States Patent [19]

Okuyama et al.

[11] Patent Number: 5,070,237
[45] Date of Patent: Dec. 3, 1991

[54] OPTICAL MEASUREMENT AND DETECTION SYSTEM

[75] Inventors: Takashi Okuyama; Masatoshi Iwama, both of Tokyo, Japan

[73] Assignee: Asahi Kogaku Kogyo K.K., Tokyo, Japan

[21] Appl. No.: 482,627

[22] Filed: Feb. 21, 1990

[30] Foreign Application Priority Data

| May 16, 1989 | [JP] | Japan | 1-121791 |
| May 16, 1989 | [JP] | Japan | 1-121792 |
| May 16, 1989 | [JP] | Japan | 1-121794 |
| May 16, 1989 | [JP] | Japan | 1-121796 |

[51] Int. Cl.$^5$ .......................................... H01J 5/16
[52] U.S. Cl. ............................... 250/227.31; 250/560; 356/386
[58] Field of Search ................... 250/227.31, 560, 562, 250/563, 571, 572, 235, 236, 327.2 F; 356/383–387, 237

[56] References Cited

U.S. PATENT DOCUMENTS

| 4,002,919 | 1/1977 | Linard | 250/560 |
| 4,371,897 | 2/1983 | Kramer | 250/227.31 |
| 4,873,438 | 10/1989 | Hosoi et al. | 250/327.2 F |
| 4,931,637 | 6/1990 | Succari et al. | 250/235 |

Primary Examiner—David C. Nelms
Attorney, Agent, or Firm—Sughrue, Mion, Zinn Macpeak & Seas

[57] ABSTRACT

An optical inspection system uses a fluorescent optical fiber to receive detection light and generate fluorescent light which then travels the length of the fiber and is detected at one or both ends thereof.

19 Claims, No Drawings

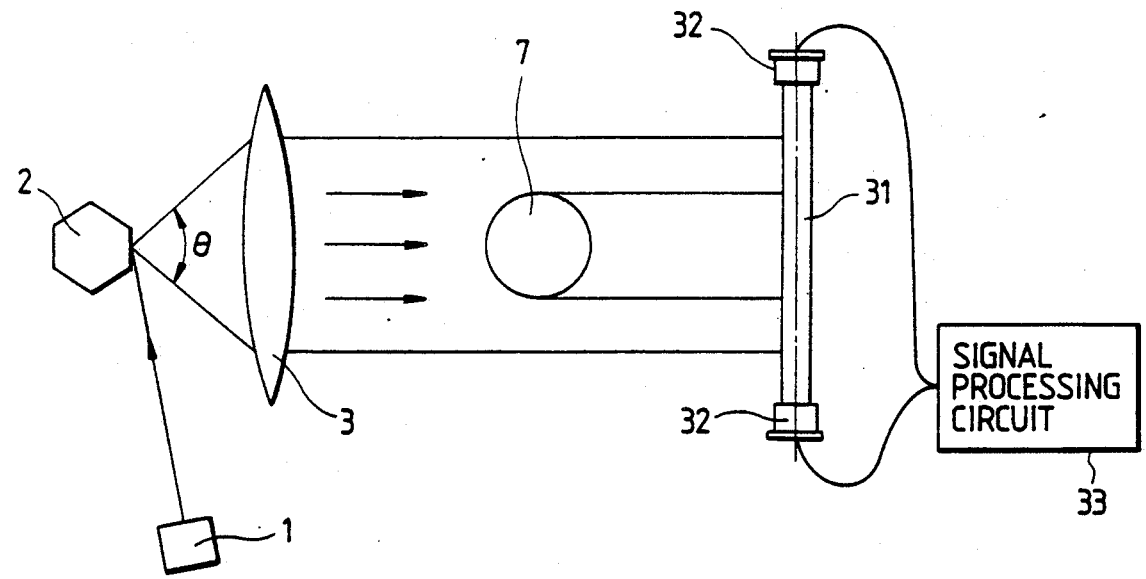

OPTICAL MEASUREMENT AND DETECTION SYSTEM

BACKGROUND OF THE INVENTION

This invention relates to measuring devices for measuring of an object under test, e.g., a baggage sorting system, a printed circuit board inspection system, or any device for measuring dimensions or other characteristics of objects based on transmission or reflection of light.

FIG. 2 shows the arrangement of a conventional measuring device. In this device, a laser beam emitted from a light source 1 such as a semiconductor laser is applied to a rotary polygonal mirror 2 forming a scanning section, where it is reflected. The rotary polygonal mirror 2 is rotated by a motor (not shown) or the like, so that the direction of reflection of the laser beam is changed over a certain range of angles ($\theta$). This causes the beam to be swung in a plane parallel to the surface of the drawing at a certain speed, so that scanning with the laser beam is carried out.

The scanning laser beam is applied to a lens 3 consisting of a convex lens or an $f\theta$ lens. The rotary polygonal mirror 2 is positioned at the focal point of the lens 3, and therefore rays of light emerging from the lens 3 are in parallel with one another irrespective of their scanning positions. The laser beam emerging from the lens 3 is applied to a convex lens 4, so that it is focused on a photodetector 5.

An object 7 under test is positioned between the lens 3 and the convex lens 4, so that a part of the laser beam is blocked by the object 7 and is not applied to the photodetector 5. Hence, by measuring the time for which the output level of the photodetector is decreased, the vertical length (in FIG. 2) of the object 7 can be determined.

A problem with a device of this type is that the use of the convex lens 4 to focus the light on a single photo sensor makes the device bulky and increases the manufacturing cost, and further it is difficult to perform measurements with high accuracy because of the aberration of the convex lens 4.

In a conventional baggage handling system, a scanning beam is typically not used, but instead the light source is a beam of predetermined width. Rather than using a convex lens and a single photodetector, the light receiving section is a photodetector array made up of a number of photodetectors arranged in a straight vertical line. As the baggage is conveyed between the light source and photodetector array, the quantity of light intercepted corresponds to the size of the baggage.

Even in this case, however, the measuring device is not only intricate in construction, because it includes the wiring, but is also high in manufacturing cost.

The present invention also relates to an inspecting apparatus for inspecting foreign matters attached to an iron plate, a film, etc., or for detecting defects thereof and positions, dimensions, etc., of parts arranged on a substrate. FIG. 9 shows the construction of a conventional inspecting apparatus as an example. In this figure, reference numeral 61 is an object to be inspected such as an iron plate, a film, etc., and reference numeral 62 is a photodetector array in which a plurality of photodetectors are linearly arranged.

An object 61 is irradiated with a laser beam and the reflected light is detected by photodetector array 62. When foreign matters such as dust, dirt, etc., are attached to object 61, or when there are defects such as flaws, cracks, etc., on object 61, the amount of reflected light from the dirty or defective portion is different from the amount of light reflected from the normal portion. Accordingly, the object can be inspected by this change in the amount of light. The inspected object is scanned by the laser beam in the direction of arrow A in FIG. 9 and is moved in the direction of arrow B. Thus, the entire object 61 can be inspected.

However, in such a conventional apparatus by using photodetector array 62, the wiring processing with respect to the individual photodetectors becomes complicated and the apparatus becomes large as the length of the array becomes long. Further, there are variations in characteristics, and a dead band, i.e., a region of insensitivity, may exist between adjacent photodetectors. Accordingly, it is necessary to arrange the respective light-receiving elements such that the adjacent photodetectors partially overlap each other, or arrange a diffusion plate in front of the photodetectors. Thus, it is difficult to perform an accurate and fine inspection, and the apparatus becomes complicated and expensive.

Further relating to printed circuit boards, there are various kinds of design rules regarding the width of a conductive portion (pattern), the interval between the conductive portions, land diameter, etc. A printed circuit board detecting apparatus of the type shown in FIG. 9 may be used to detect whether or not a printed circuit board having a predetermined pattern thereon meets these design rules. To inspect the printed circuit board, it is scanned by a laser beam and the reflected light is received by a photodetector array in which a plurality of photodetectors are linearly arranged. The conductive portion which is made of copper, etc. and a base material portion which is made of glass. epoxy resin, etc., are different from each other in the directivity of the reflected light. Normally, the conductive portion is higher in reflectance than the base material portion, so that it detects a larger amount of the reflected light. Accordingly, the pattern of the printed circuit board can be inspected from the change in output of the photodetector array. It is also known to have the reflected light at each scanning position incident onto a single photodetector by way of a condenser lens arranged in front of this single photodetector.

The design rule inspection apparatus using a detector array suffers from the same problems discussed above with respect to the flaw detection apparatus. For the design rule inspection apparatus which uses a condenser lens to converge the reflected light onto one photodetector, it is necessary to employ a large-sized condenser lens to scan at once a wide range of the printed circuit board. Hence, the apparatus becomes large and expensive.

In view of the foregoing, an object of this invention is to provide a measuring device which is small in size and low in manufacturing cost, and permits measurement with high accuracy.

It is a further object of the invention to provide a compact and inexpensive object inspection system which can perform an accurate and fine inspection at once over a wider range of an object.

SUMMARY OF THE INVENTION

The foregoing and other objects of the invention have been achieved by the provision of a measuring device comprising: a light source for emitting light; a scanning section for swinging a light beam from the light source in a predetermined range of direction angles; a lens for making light beams from the scanning section parallel with one another irrespective of incident angles thereof; a fluorescent optical fiber which is spaced by a predetermined distance from the lens so that an object under measurement can be positioned between the lens and fiber, and which is arranged in a scanning plane of the light beams emerging from the lens in such a manner that the fluorescent optical fiber is substantially perpendicular to the optical axis of the light beams; a photodetector for receiving light emerging from an end face of the fluorescent optical fiber; and a decision circuit for receiving an output of the photodetector, to determine the length of the object under measurement.

A laser beam provided by the light source is applied to the lens while being swung by the scanning section, so that the laser beams emerging from the lens are made parallel with one another irrespective of their incident angles. The laser beams emerging from the lens are applied to the side of the fluorescent optical fiber. The optical fiber contains fluorescent material, which emits fluorescent light in response to the incident laser beam. The fluorescent light thus emitted is transmitted inside the fluorescent optical fiber, and is received by the photodetector provided on the end face of the fluorescent optical fiber. The output of the photodetector is utilized to determine the length of the object. Accordingly, the measuring device of the invention can measure the length of an object accurately without increasing its size or its manufacturing cost.

In the case of a system for sorting baggage or other objects by size as they are conveyed through a size detector, the light source and scanning section are replaced by a light source, e.g., a linear fluorescent lamp, emitting a beam of predetermined width, with the fluorescent optical fiber arranged in a direction parallel to the width of the beam. A part of the light beam incident to the fluorescent optical fiber is intercepted by the object. Therefore, the height of the object corresponds to the quantity of light incident on the fluorescent optical fiber, and under the condition that the speed of the movement of the object is a constant, the width of the object corresponds to the period of time for which the light beam is intercepted by the object. Accordingly, the size of the object can be determined from the variation and rates of variation of the outputs of the light receiving elements and the period of time mentioned above.

A further embodiment of the present invention resides in an inspecting apparatus comprising a light source for emitting light for inspection; a scanning section using the light emitted from said light source to scan an object in a predetermined direction; a fluorescent optical fiber arranged substantially parallel to the scanning direction of the scanning section so as to receive light reflected from the object at a side face of the fluorescent optical fiber; and a photodetector arranged at at least one end portion of the fluorescent optical fiber and receiving fluorescent light generated within the fluorescent optical fiber.

Light emitted from the light source irradiates on the object through the scanning section composed of a polygonal mirror, etc. The reflected light from the object is incident on a side face of the fluorescent optical fiber which is arranged in parallel to the scanning direction of the incident beam. The fluorescent optical fiber generates a fluorescent light in response to the light incident on it, and this fluorescent light travels along the fiber and is detected by the photodetector. The fluorescent optical fiber is inexpensive, and it is easy to manufacture a long fluorescent optical fiber having uniform characteristics. Accordingly, a compact and inexpensive apparatus is realized which can inspect an object over a wider range at one time, and which can perform accurate and fine inspection.

A still further embodiment of the present invention resides in a printed circuit board inspecting apparatus comprising: a light source for emitting an inspection light beam; a table for moving a printed circuit board in a predetermined direction; a scanning section for scanning the printed circuit board, with the light emitted from the light source in a direction approximately perpendicular to the moving direction of the table; a fluorescent optical fiber arranged approximately parallel to the scanning direction by the scanning section so as to receive the reflected light from the printed circuit board through a side face of the fiber and a photodetector disposed on at least one end face of the fluorescent optical fiber.

BRIEF DESCRIPTION OF THE DRAWINGS

The invention will be more clearly understood from the following description in conjunction with the accompanying drawings, wherein.

DETAILED DESCRIPTION OF THE PREFERRED EMBODIMENT

Figure 1:
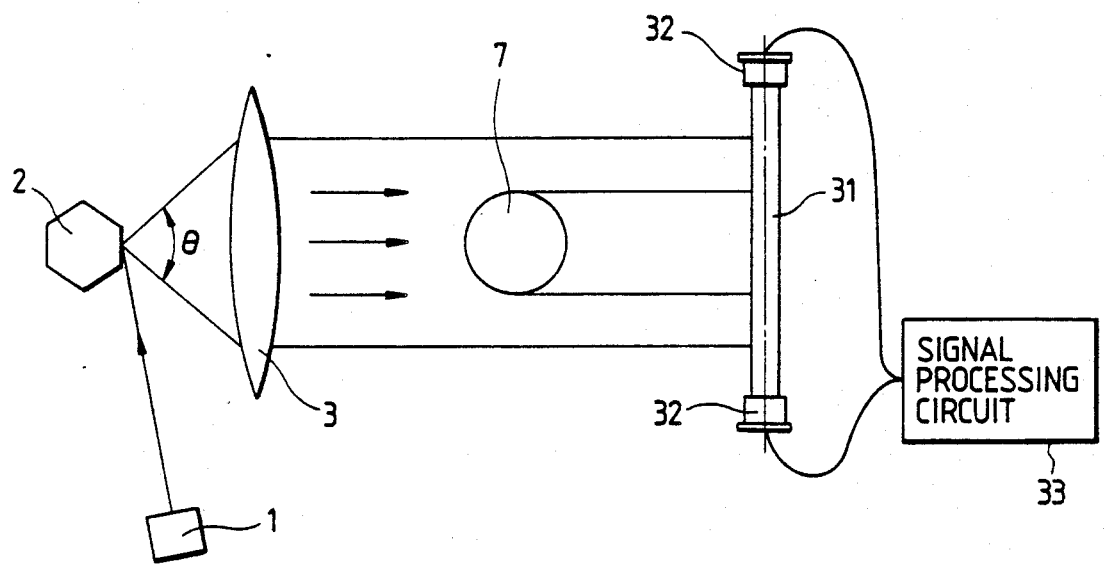
FIG. 1 is a plane view showing an optical system in a measuring device according to this invention.
Figure 2:
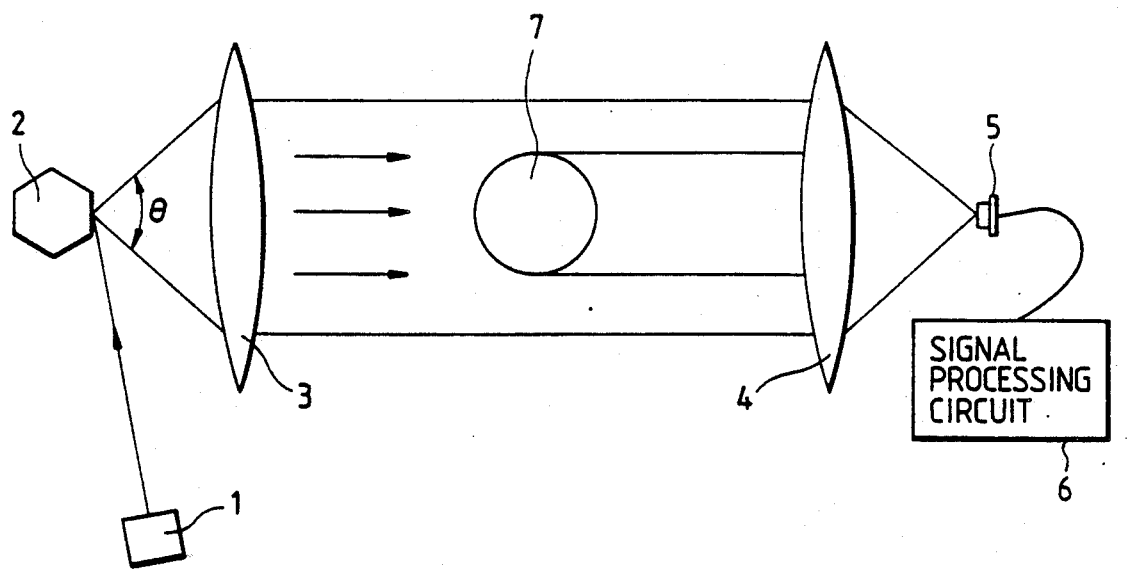
FIG. 2 is a plan view of an optical system in a conventional measuring device.

FIG. 1 shows the arrangement of an optical system in one example of a measuring device according to the invention. In FIG. 1, parts functionally corresponding to those already described in FIG. 2 are therefore designated by the same reference numerals or characters.

In FIG. 1, reference numeral 31 designates a fluorescent optical fiber which is arranged in the scanning plane (parallel with the drawing surface) of the laser beam in such a manner that it is perpendicular to the optical axis of the laser beam. A photodetector 32 is provided at at least one end of the fluorescent optical fiber 31 (in the case of FIG. 1, there is a photodetector provided at each end of the optical fiber). A signal processing circuit 33 is provided for processing the outputs of the light receiving elements 32.

Figure 3:
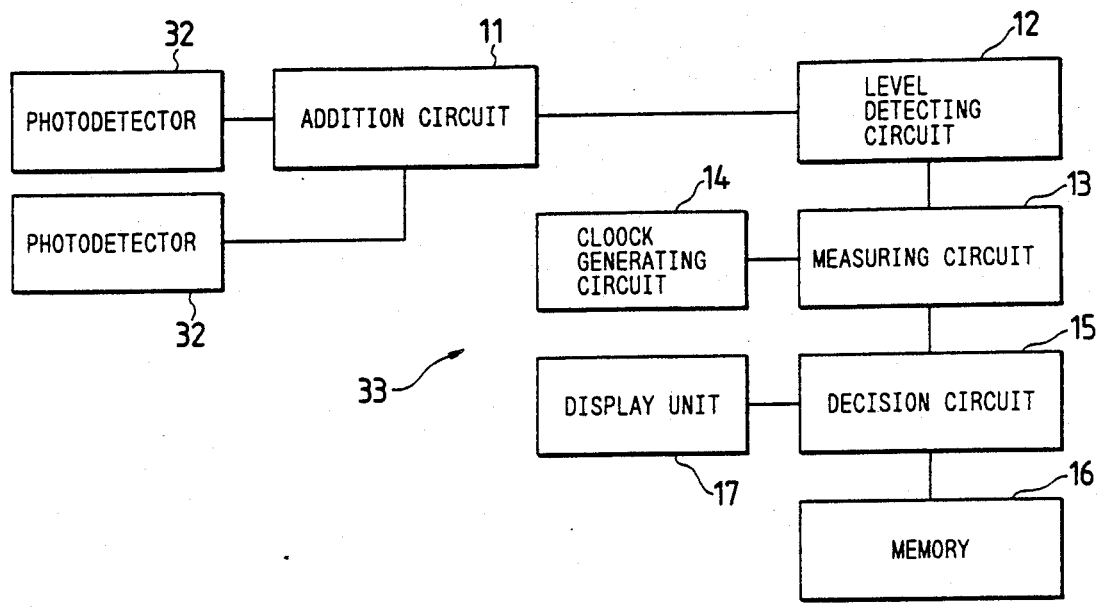
FIG. 3 is a block diagram showing a signal processing system in the measuring device according to the invention.

FIG. 3 is a block diagram showing the signal processing circuit 33 in detail. In FIG. 3, reference numeral 11 designates an addition circuit for adding the outputs of the two photodetectors 32. The addition circuit 11 is omitted, in the case where only one photodetector 32 is employed. Further in FIG. 3, reference numeral 12 designates a level detecting circuit for detecting the level of an output signal of the addition circuit 11. A measuring circuit 13 counts the clock pulses provided by a clock generating circuit 14, to measure the time for which the output of the detecting circuit is held at a predetermined level. A decision circuit 15 compares the output of the measuring circuit 13 with the data stored in a memory 16, to determine the length of an object 7 under test, and a display the unit 17 displays data corresponding to the length thus determined.

Figure 4:
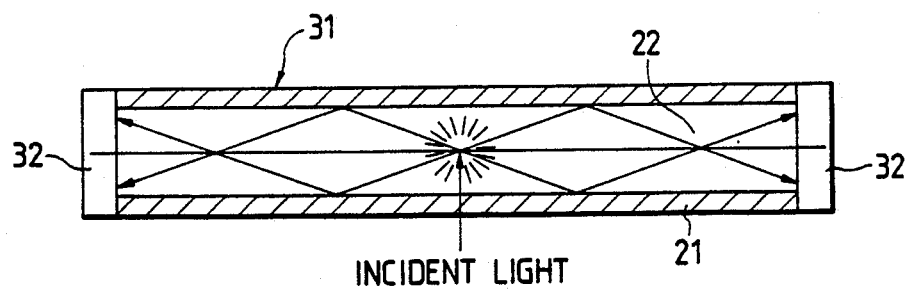
FIG. 4 is a longitudinal sectional view showing one example of a fluorescent optical fiber in the measuring device according to the invention.
Figure 5:
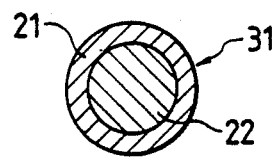
FIG. 5 is a cross sectional view of the fluorescent optical fiber shown in FIG. 4.

The fluorescent optical fiber 31 is constructed as shown in FIGS. 4 and 5.

In FIGS. 4 and 5, reference numeral 21 designates a first member made of glass or resin, the member 21 being in the form of a cylindrical pipe in this embodiment; and 22 designates a second member made of glass or resin inside the member 21. The second member 22 has a higher refractive index than the first member 21. In addition, fluorescent material is uniformly dispersed in the second member 22 to absorb light incident thereto.

Light entering the fluorescent optical fiber 32 through its side penetrates the member 21, thus reaching the second member 22 which contains the fluorescent material as was described above. Thus, the incident light is absorbed by the fluorescent material, which in turn emits fluorescent light.

As described above, the refractive index of the second member 22 is larger than that of the first member 21. Therefore, the fluorescent light produced by the second member 22 cannot penetrate the first member 21, being instead reflected by the inner wall of the first member 21. As a result, the fluorescent light is transmitted toward the right and left ends of the fluorescent optical fiber and is detected by the photodetectors 32 provided on the right and left end faces of the second member 22.

The outputs of the two photodetectors 32 are applied to the addition circuit 11, where they are together. The output of the circuit 11 is supplied to the level detecting circuit 12, which detects the level of the input signal. On the other hand, the measuring circuit 13 counts the clock pulses applied thereto by the clock generating circuit 14 during the period for which the level detecting circuit 12 detects a lower level signal, which is provided when the light beam is blocked by the object 7 and is not applied to the fluorescent optical fiber 31, thereby determining the length of the time period. The length (or the number or the clock pulses) determined by the measuring circuit 13 is applied to the decision circuit 15.

A table indicating the object's length as a function of clock pulse counts is stored in the memory 16 in advance. The decision circuit 15 compares the data clock pulse counts received from the measuring circuit 13 with the data stored in the memory 16, to read the corresponding length data and to display it on the display unit 17.

Figure 6:
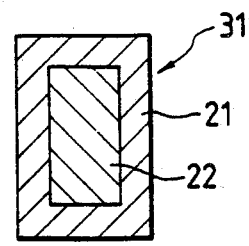
FIG. 6 is a cross sectional view showing another example of the fluorescent optical fiber according to the invention.

In the above-described embodiment, the fluorescent optical fiber 31 is cylindrical. However, it may be substantially rectangular in section as shown in FIG. 6, or it may be a quadrangular prism.

As was discussed above, in the measuring device of the invention, the light beam emerging from the lens is applied to the side of the fluorescent optical fiber, and an object to be tested is positioned between the lens and the optical fiber. Therefore, the measuring device can be reduced both in size and in manufacturing cost. Furthermore, in the measuring device of the invention, the scanning light beam is applied to the fluorescent optical fiber as it is (i.e., without being converged), and therefore the measurement can be achieved with higher accuracy.

Figure 7:
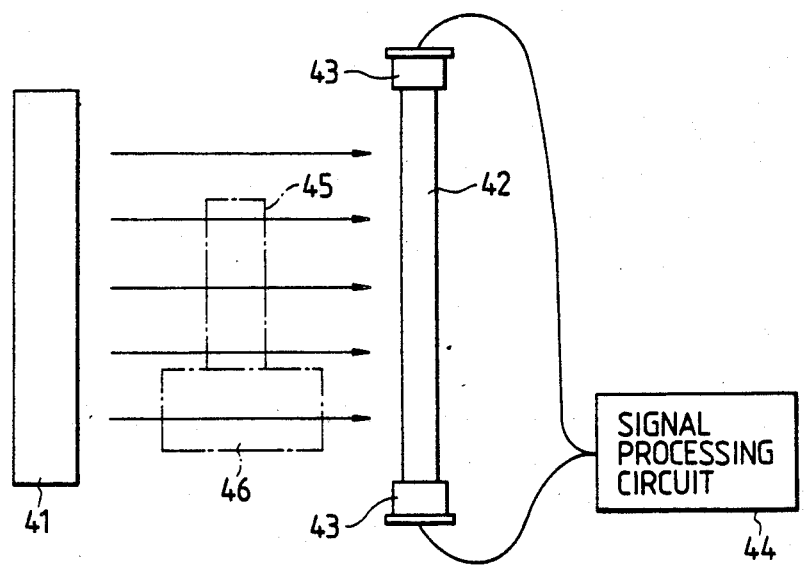
FIG. 7 is a side view showing an optical system for a baggage sorting system according to the present invention.

FIG. 7 shows the arrangement of one example of the application of this invention to a system for sorting baggage or other moving objects by size. In FIG. 7, reference numeral 41 designates a light source which may be, for instance, a linear fluorescent lamp. A fluorescent optical fiber 42 is spaced at a predetermined distance from the light source 41 in such a manner that it is in parallel with the light source 41. A photodetector 43 is provided at at least one end of the fluorescent optical fiber 42 (Shown at both ends in the example of FIG. 7). A signal processing circuit 44 processes the outputs of the photodetectors 43.

Further in FIG. 7, reference numeral 45 designates an object under measurement such as a piece of baggage which is disposed between the light source 41 and the fluorescent optical fiber 42. The object 45 is moved in a direction perpendicular to the surface of the drawing by means of a belt 46. The device may also be so modified that the object 45 is held stationary, whereas the light source 41 and the fluorescent optical fiber 42 are moved by moving means such as a belt.

Figure 8:
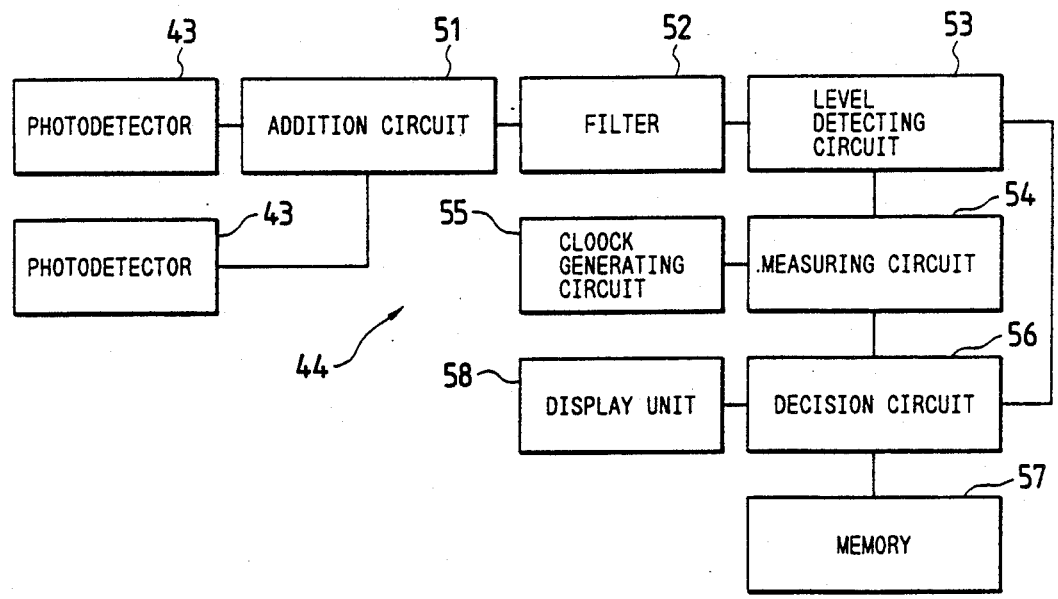
FIG. 8 is a block diagram showing the arrangement of a signal processing circuit in the measuring device of FIG. 7.
Figure 9:
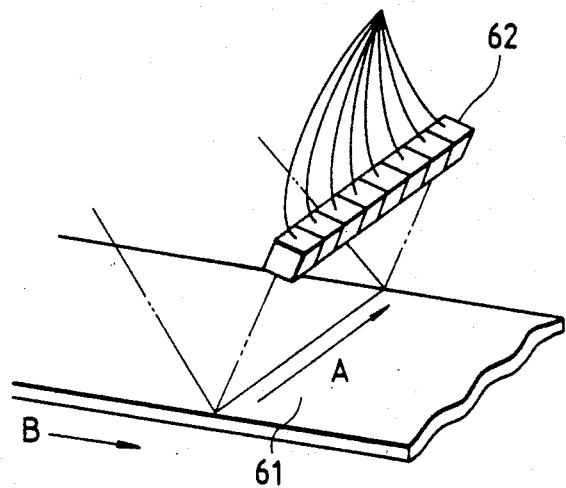
FIG. 9 is a perspective view of an optical system of a conventional inspecting apparatus.

FIG. 8 is a block diagram showing the arrangement of the signal processing circuit 44. In FIG. 8, reference numeral 51 designates an addition circuit for adding the outputs of the two photodetectors 43. However, the addition circuit 51 may be omitted when only one photodetector is employed. Further in FIG. 8, reference numeral 52 designates a filter which removes frequency components other than 100 Hz when the light source 51 is operated on a 50 Hz power source, or frequency components other than 120 Hz when the light source is operated on a 60 Hz power source. A level detecting circuit 53 detects the level of the output signal of the filter 52, and a measuring circuit 54 counts clock pulses outputted by a clock generating circuit 15, to measure the time for which the output of the level detecting circuit 53 is held at a predetermined level. A decision circuit 56 compares the outputs of the level detecting circuit 53 and the measuring circuit 54 with reference values stored in a memory 57, to determine the size of the object under measurement, and a display unit 58 to displays data on the size thus determined.

The light beam output from the light source 41 is applied to the fluorescent optical fiber 42. When there is no object 45 between the light source 41 and the fluorescent optical fiber 42, almost all light beam emitted towards the fluorescent optical fiber 42 reaches the fiber 42. On the other hand, when an object 45 is disposed between the light source 41 and the fluorescent optical fiber 42, at least a part of the light beam is intercepted by the object 45, and is not applied to the fluorescent optical fiber 42.

The fluorescent optical fiber 42 may be constructed in generally the same manner as shown in FIGS. 4–6. The quantity of fluorescent light produced by the fiber and detected at one or both ends thereof corresponds to the quantity of incident light thereon. The quantity of incident light decreases as the height (or the vertical length in FIG. 7) of the object 45 under measurement increases. The time for which the incident light is intercepted increases as the width (or the length in a direction perpendicular to the surface of the drawing in FIG. 7) of the object 45, which is moved in a direction perpendicular to the surface of the drawing, increases. Each of the photodetectors 43 receives the fluorescent light transmitted inside the fiber and converts it into an electrical signal. Therefore, the outputs of the photodetectors 43 include data on the height and width of the object 45 under measurement.

The outputs of the two photodetectors 43 are added in addition circuit 51. The addition output is applied to the filter 12. The light source 41 is turned on and off at a frequency which is two times the frequency of the drive power source. Therefore, when the frequency of the drive power source is 50 Hz, the output of the addition circuit contains a 100 Hz frequency component; and when it is 60 Hz, the output contains a 120 Hz frequency component. Frequency components other than 100 Hz or 120 Hz frequency component are eliminated by the filter 52 because they are not attributable to the light source 41.

The output of the filter 52 is applied to the level detecting circuit 53, where its level is detected. On the other hand, the measuring circuit 54 counts clock pulses applied thereto by the clock generating circuit 55 for the period during which the level detecting circuit 53 is detecting a signal having a predetermined level, to thereby measure the length of this period. The signal level detected by the level detecting circuit 53 and the period (or the number of clock pulses) measured by the measuring circuit 54 are supplied to the decision circuit 56.

A data table indicating object heights with detected signal levels, and a data table indicating object widths with measured clock pulse numbers is stored in the memory 57. The decision circuit 56 compares the output data of the level detecting circuit 53 and the measuring circuit 54 with the data on the tables stored in the memory 57, reads the corresponding data for the object height and width, and displays them on the display unit 58.

In the case where, depending on its size, the object is removed from the belt 46 when it comes to a predetermined position, the results of the decision by the decision circuit 56 are applied to the object unloading units (not shown) which are provided at predetermined positions, so that each object unloading unit operates to unload an object from the belt 6 when it is determined that the object at the position of the unloading unit is to be handled by the unloading unit.

In order to prevent erroneous operations due to light reflected from the surrounding walls or the like, slits or the like may be provided at the rear of the light source 41 and/or in front of the fluorescent optical fiber 42.

In the baggage or object size measurement system of FIGS. 7 and 8, the output light beam of the light source is applied to the fluorescent optical fiber, and an object to be measured is positioned between the light source and the fluorescent optical fiber. Therefore, the measuring device can be simplified in construction, and decreased in manufacturing cost. In addition, the elongated light source and the fluorescent optical fiber can be readily obtained, and therefore it follows that even a relatively large object can be measured with the measuring device of the invention.

Figure 10:
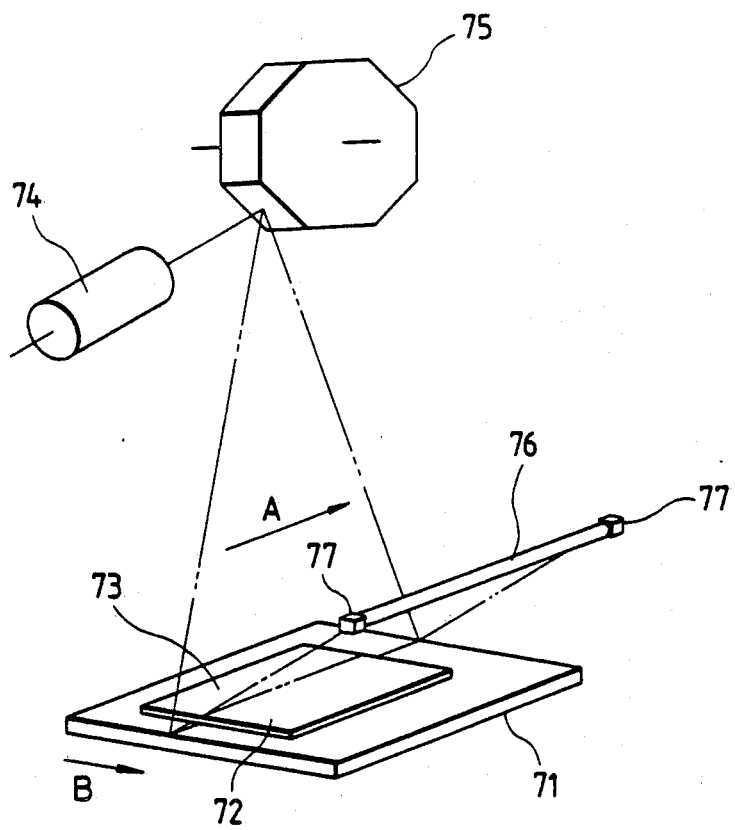
FIG. 10 is a perspective view of an example of an optical system of an inspecting apparatus according to the present invention.

FIG. 10 shows the construction of an optical system of an inspecting apparatus according to the present invention. In this figure, table 71 is moved by a drive means (not shown) in the direction of arrow B in FIG. 10, and object 72 is arranged on this table 71. Reference numeral 73 shows a foreign matter attached to object 72.

Light source 74, such as a semiconductor laser, etc., emits a laser beam. A scanning section comprising rotary polygonal mirror 75 reflects the laser beam to scan the object in the direction of arrow A. Fluorescent optical fiber 76 is arranged approximately parallel to the scanning direction by rotary polygonal mirror 75. Photodetector 77 is arranged on at least one end (both ends in this embodiment) of fluorescent optical fiber 76.

Figure 11:
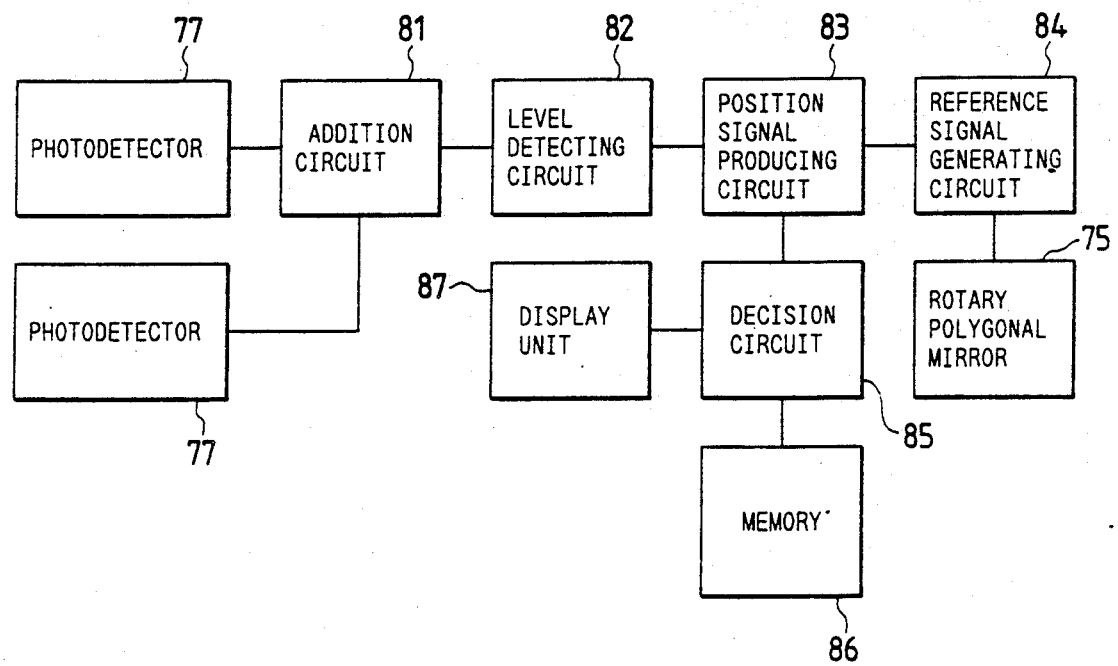
FIG. 11 is a block diagram of a signal processing system in the inspecting apparatus of FIG. 10.

FIG. 11 is a block diagram of signal processing circuitry for an inspecting apparatus according to FIG. 10. In this figure, addition circuit 81 adds the outputs of two photodetectors 77 to each other, and may be omitted when only one photodetector 77 is used. Level detecting circuit 82 detects the level of an output signal of addition circuit 81. Reference signal generating circuit 84 generates a reference signal which is synchronized with the rotation of rotary polygonal mirror 75 and corresponds the rotary speed thereof. Position signal producing circuit 83 converts a signal on the time axis outputted from level detecting circuit 82 to a position signal corresponding to a position on object 72 in accordance with a reference signal outputted from reference signal generating circuit 84. Decision circuit 85 compares the position signal produced by position signal producing circuit 83 with a reference value stored in memory 86. Display unit 87 indicates the decision result of decision circuit 85.

The operation of the above inspecting apparatus will now be described.

The laser beam emitted from light source 74 is reflected by rotary polygonal mirror 75 and is incident to object 72, placed on table 71. The object is scanned by this laser beam corresponding to the rotation of rotary polygonal mirror 75 in the direction of arrow A in FIG. 10. Since table 71 is moved in the direction of arrow B approximately perpendicular to the direction of arrow A, the entire object 72 is scanned by the laser beam.

The laser beam reflected by object 72 is incident on fluorescent optical fiber 76 from a side face thereof. Fluorescent optical fiber 76 is preferably constructed as shown in FIGS. 4 and 5. Fluorescent light is transmitted internally in the fiber towards left and right end faces where it is detected by photodetectors 77 (32 in FIG. 4) arranged on the left and right end faces of the fiber.

Figure 12A:
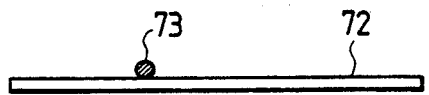
FIGS. 12A and 12B are respectively a side view of the object inspected by the system of FIG. 10, and a waveform of a detecting output provided when the object is scanned.
Figure 12B:
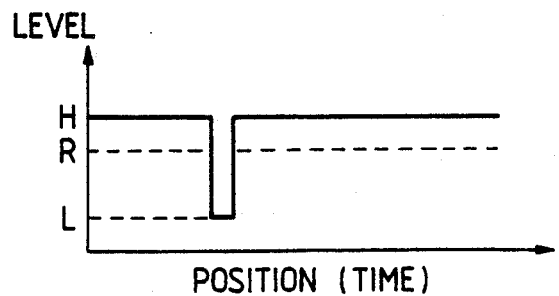

As shown in FIGS. 12A and 12B, when a portion of object 72 to which foreign matter 73 is attached is scanned, the output levels of photodetectors 77 at the time the foreign matter 73 is scanned are reduced in comparison to the outputs during the remaining scanning interval.

The outputs of two photodetectors 77 are added to each other by addition circuit 81 and the added level is detected by level detecting circuit 82. Position signal producing circuit 83 converts the output signal from the level detecting circuit 82, which is on the time axis, to a position signal corresponding to a position on object 72, with reference to a signal reflecting the scanning speed of rotary polygonal mirror 75 which is inputted from reference signal generating circuit 84. Accordingly, the signal outputted from position signal producing circuit 83 is a signal corresponding to the real position (distance) on object 72. This signal is compared in decision circuit 85 with reference values R stored in memory 86 in advance.

Reference values R stored in memory 86 are set between detection level H for a portion of object 72 without foreign matter, and detection level L with foreign matter 73. Accordingly, it is possible to judge whether or not there is foreign matter 73 by comparing the above-mentioned signal with reference values R. The judging results are displayed by display unit 87.

Fluorescent optical fiber 76 is inexpensive, and it is easy to manufacture a long, thin fluorescent optical fiber having uniform characteristics. Accordingly, an accurate and fine inspection can be performed at one time over a wide range of the object.

Figure 13:
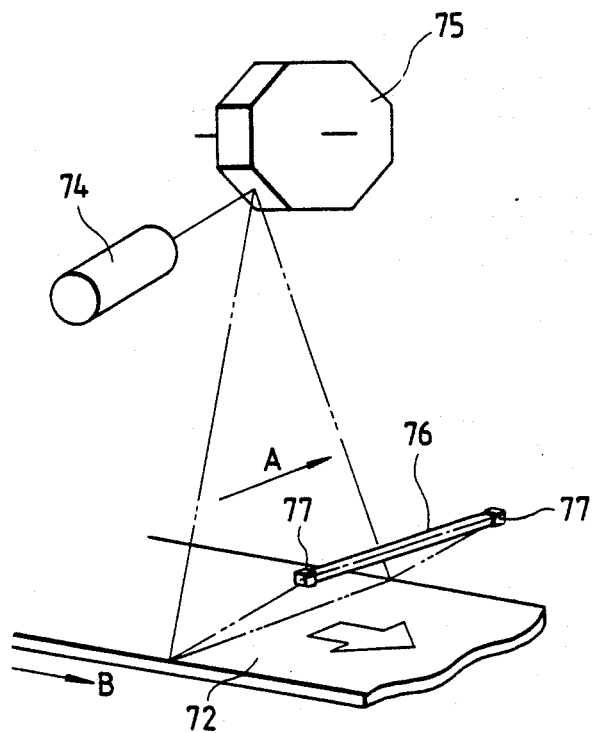
FIGS. 13 and 14 are perspective views of the inspecting apparatus of the present invention when another object is inspected.

FIG. 13 shows a case in which defects such as flaws, cracks, etc., of object 72 such as an iron plate, a film, etc., are detected. In this case, the relatively long object 72 is moved in the direction of arrow B by suitable conveying means (not shown).

In this case, too, the detection output for the portions of the object at which there are flaws, cracks, etc., is reduced in comparison with the detection output at other times. Accordingly, the defects can be detected in a manner similar to the case of the foreign matter described above.

Figure 14:
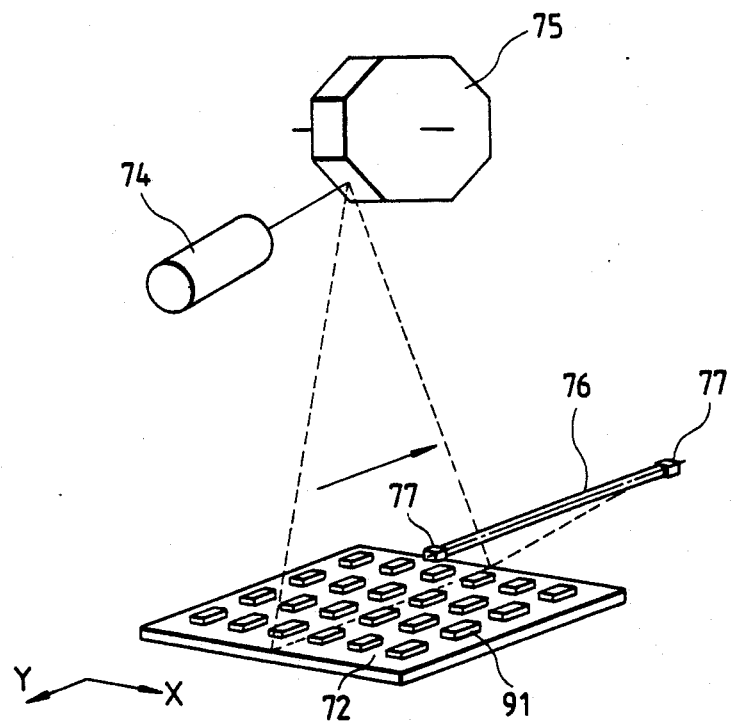

FIG. 14 shows a case in which the position of part 91 attached to object 72 composed of, e.g., a printed circuit board is detected.

Figure 15A:
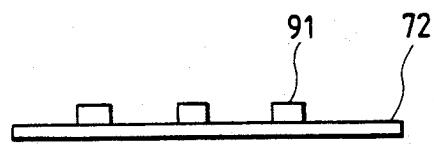
FIGS. 15A, 15B, and 15C are a side view of the object in FIG. 14, a waveform of the detection output provided when the object is inspected, and a waveform of a reference position signal to be compared, respectively.
Figure 15B:
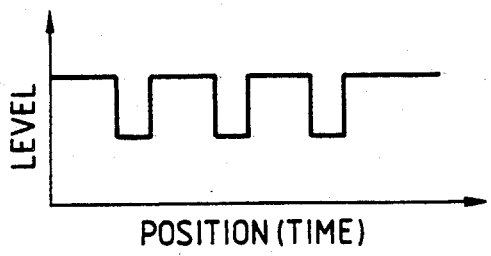
Figure 15C:
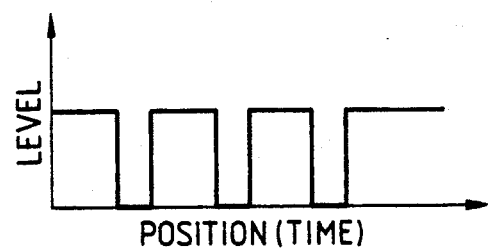

When object 72 bearing parts 91 as shown in FIG. 15A is scanned, the detection output at this time is provided as shown in FIG. 15B. Namely, the detection level at part 91 is reduced (or increased) in comparison with that for the other portions of the object 72. The position corresponding to the changed detection level is known to be the attaching position of the above part. Therefore, a shift or error in attaching position, etc., can be detected by comparing this information with data on the attaching position stored in memory 86 as shown in FIG. 15C.

In the above embodiments, fluorescent optical fiber 76 is approximately cylindrical, but may be approximately rectangular in cross section and therefore the fluorescent optical fiber can be formed in the shape of a square pole as shown in FIG. 6.

Figure 16:
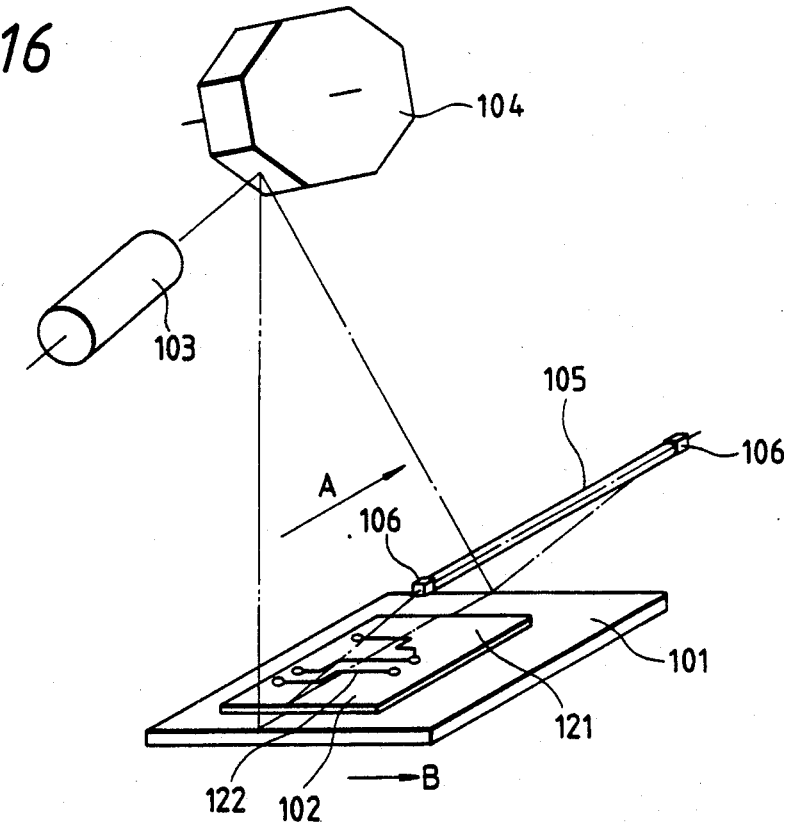
FIG. 16 is a perspective view of an optical system in a printed circuit board inspecting apparatus according to a further embodiment of the present invention.

FIG. 16 shows the application of the present invention to a design rule inspection system. In this figure, table 101 is moved by drive means (not shown) in the direction of arrow B and printed circuit board 102 to be inspected is placed on this table 101. A conductive portion 122 made of copper or the like is formed on base material portion 121 made of glass, epoxy resin, etc. Light source 103, such as semiconductor laser, emits a laser beam toward rotary polygonal mirror 104 which reflects the laser beam to scan printed circuit board 102 in the direction of arrow A. Fluorescent optical fiber 105 is arranged substantially parallel to the scanning direction of rotary mirror 104. The fiber 105 is constructed in the manner shown in FIGS. 4-6. Photodetector 106 is arranged on at least one end (both ends in this embodiment) of fluorescent optical fiber 105.

The signal processing circuitry for this embodiment is essentially the same as that shown in FIG. 11. Decision circuit 85 compares the position signal produced by position signal producing circuit 83 with data on design rules, etc. stored in memory 86. Display unit 87 indicates the decision results. The operation of the above printed circuit board inspecting apparatus will now be described. The laser beam emitted from light source 103 is reflected by rotary polygonal mirror 104 and is incident onto printed circuit board 102 placed on table 101. The printed circuit board is scanned by this laser beam in accordance with the rotation of rotary polygonal mirror 104 in the direction of arrow A in FIG. 16. Since table 101 is moved in the direction of arrow B approximately perpendicular to the direction of arrow A, the entire printed circuit board 102 is scanned by the laser beam. The laser beam reflected by print substrate 102 is incident onto fluorescent optical fiber 105 through a side face thereof. The fluorescent light is transmitted towards left and right end faces of the fiber. Accordingly, this fluorescent light is detected by photodetectors 106 arranged on the left and right end faces of the fiber.

Figure 17A:
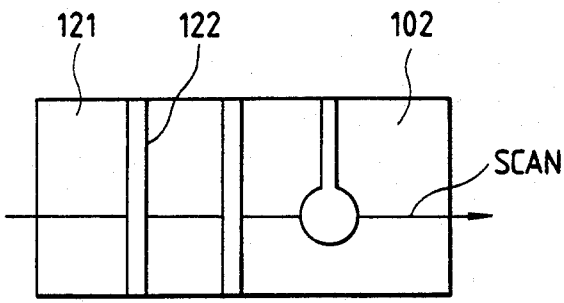
FIGS. 17A and 17B are plane views of the printed circuit board inspected in the printed circuit board inspecting apparatus of FIG. 16, and a waveform of a detection output provided when the printed circuit board is scanned.
Figure 17B:
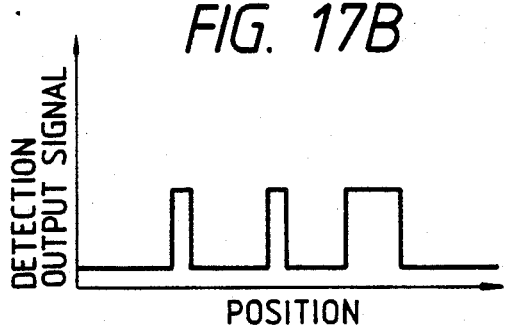

While base material portion 121 of printed circuit board 102 is formed of glass, epoxy resin, etc., conductive portion 122 is formed of copper, etc. Therefore, according to this material difference, conductive portion 122 exhibits a greater reflectance than base material portion 121, so that a larger amount of reflected light is incident onto fluorescent optical fiber 105. The generated amount of the fluorescent light corresponds to the amount of the incident light. As a result, as shown in FIGS. 17A and 17B, when printed circuit board 102 is scanned by the laser beam, the output of photodetector 106 in the case of conductive portion 122 is greater than that in the case of base material portion 122.

As before, the signal outputted from position signal producing circuit 83 is a signal corresponding to the real position (distance) on printed circuit board 2. This signal is compared in decision circuit 85 with the design rules, etc. stored in memory 86 in advance. Namely, it is judged whether or not the signal outputted from producing circuit 83 conforms to the data stored in memory 86, which related to the width is of conductive portion 122, the distance between two conductive portions 122, etc. The judging results are displayed by display unit 87.

Figure 18:
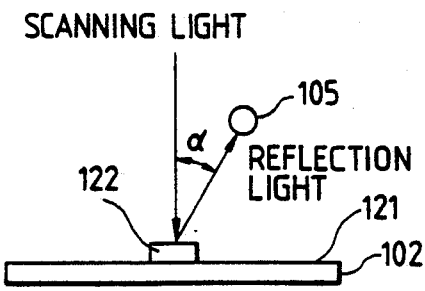
FIGS. 18 and 19 are side views for explaining the relation between the incident light and the reflected light with respect to the printed circuit board in the apparatus of FIG. 16.
Figure 19:
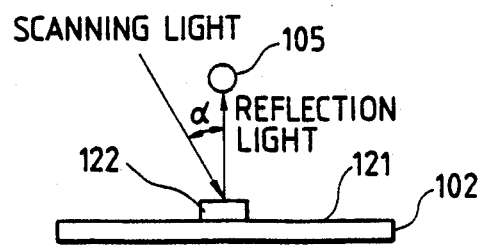

FIGS. 18 and 19 show the relation between the incident light and the reflected light with respect to printed circuit board 102. In the arrangement of FIG. 18, the laser beam is incident onto printed circuit board 102 in a direction approximately perpendicular thereto. The light reflected and inclined by predetermined inclination angle α with respect to the incident light is detected by fluorescent optical fiber 105. On the other hand, in the arrangement of FIG. 19, fluorescent optical fiber 150 is arranged such that the laser beam is incident onto printed circuit board 102 at incident angle α and this fluorescent optical fiber receives the laser beam reflected by printed circuit board 102 in a direction approximately perpendicular thereto.

Since the directivity and amount of the reflected light will depend on the materials of conductive portion 122 and base material portion 121, the positions of rotary polygonal mirror 104 and fluorescent optical fiber 105 are selected such that the difference between signals to be obtained with these portions becomes greatest.

As before, fluorescent optical fiber 105 is approximately cylindrical in this embodiment but may be approximately rectangular in cross section as shown in FIG. 6.

It will be appreciated that various changes and modifications may be made to the preferred embodiments described above without departing from the spirit and scope of the invention as defined in the appended claims.

What is claimed is:

1. A device for examining an object to determine a characteristic thereof, said device comprising means for translating said object in a predetermined moving direction, irradiation means for irradiating said object with light, said irradiation means emitting light in a direction substantially perpendicular to said moving direction and detection means for detecting light received at a detection station, said detection means comprising:
   a fluorescent optical fiber responsive to said light received at said detection station for generating fluorescent light which travels along said fiber to at least one end thereof;
   photodetection means disposed at said one end of said fiber for generating an output indicating an amount of fluorescent light received at said one end of said fiber; and
   detection circuitry for processing the output from said photodetection means to determine said predetermined characteristic of said object.

2. A device for examining an object to determine a characteristic thereof, said device comprising irradiation means for irradiating said object with light, and detection means for detecting light received at a detection station, said detection means comprising:
   a fluorescent optical fiber responsive to said light received at said detection station for generating fluorescent light which travels along said fiber to at least one end thereof;
   photodetection means disposed at said one end of said fiber for generating an output indicating an amount of fluorescent light received at said one end of said fiber; and
   detection circuitry for processing the output from said photodetection means to determine said predetermined characteristic of said object;
   wherein said object is positioned between said irradiation means and said fluorescent optical fiber in an aligned manner; and
   wherein said irradiation means comprises a light source for emitting light, a scanning section for receiving said light from said light source and providing a scanning light beam which swings through a range of scanning angles, and a lens receiving said scanning light beam and providing a scanning light beam which traverses a scanning width in a scanning plane while maintaining a constant direction, and wherein said fluorescent optical fiber is substantially parallel to said scanning plane.

3. A device according to claim 2, wherein said scanning light beam has an optical axis substantially perpendicular to said fluorescent optical fiber.

4. A device for examining an object to determine a characteristic thereof, said device comprising irradiation means for irradiating said object with light, and detection means for detecting light received at a detection station, said detection means comprising:
   a fluorescent optical fiber responsive to said light received at said detection station for generating fluorescent light which travels along said fiber to at least one end thereof;
   photodetection means disposed at said one end of said fiber for generating an output indicating an amount of fluorescent light received at said one end of said fiber; and
   detection circuitry for processing the output from said photodetection means to determine said predetermined characteristic of said object; and
   wherein said detection circuitry comprises level detection means for providing an output corresponding to the level of the output signal of said photodetection means, determining means responsive to an output from said level detection means for generating an output representing the time interval within a scan during which the output of said level detection means is at a predetermined level, and decision means responsive to an output from said determining means and to stored data for determining said characteristic of said object.

5. A device according to claim 4, wherein said determining means determines the position of said time interval within a scanning interval.

6. A device according to claim 4, wherein said determining means determines the duration of said time interval.

7. A device according to claim 1, wherein said characteristic is size in at least one dimension.

8. A device according to claim 1, wherein said characteristic is the existence of a surface anomaly.

9. A device according to claim 1, wherein said object is a substrate and said characteristic is the location of components on said substrate.

10. A device according to claim 1, wherein said object is a substrate having a printed circuit thereon, and said characteristic is the location or dimensions of portions of said printed circuit.

11. A device according to claim 1, wherein said fluorescent optical fiber is substantially circular in cross section.

12. A device according to claim 1, wherein said fluorescent optical fiber is substantially rectangular in cross section.

13. A device for examining an object to determine a characteristic thereof, said device comprising irradiation means for irradiating said object with light, and detection means for detecting light received at a detection station, said detection means comprising:
- a fluorescent optical fiber responsive to said light received at said detection station for generating fluorescent light which travels along said fiber to at least one end thereof;
- photodetection means disposed at said one end of said fiber for generating an output indicating an amount of fluorescent light received at said one end of said fiber; and
- detection circuitry for processing the output from said photodetection means to determine said predetermined characteristic of said object;
- wherein said object is positioned between said irradiation means and said detection circuitry in an aligned manner; and
- wherein said irradiation means comprises a light source for emitting a light beam having a predetermined width in at least one direction, and wherein said fluorescent optical fiber is substantially parallel to said one direction.

14. A device according to claim 13, wherein said light beam has an optical axis substantially perpendicular to said fluorescent optical fiber.

15. A device according to claim 13, further comprising conveying means for conveying said object past said light beam in a direction transverse to said one direction, wherein said detection circuitry comprises level detection means for providing an output corresponding to the level of the output signal of said photodetection means, determining means responsive to an output from said level detection means for generating an output representing a duration during passage of said object past said light beam for which the output of said level detection means is at a predetermined level, and decision means responsive to an output from said determining means and to stored data for determining said characteristic of said object.

16. A device according to claim 15, wherein said characteristic is the dimension of said object in a direction parallel to the direction in which it is conveyed past said light beam.

17. A device according to claim 16, wherein said determining means output further represents the amount of light received by said fiber when said light beam is interrupted by said object, and wherein said characteristic further comprises the dimension of said object in a direction parallel to said one direction.

18. A device according to claim 13, wherein said detection circuitry comprises level detection means for providing an output corresponding to the level of the output signal of said photodetection means, determining means responsive to an output from said level detection means for generating an output representing the amount of light received by said fiber when said light beam is interrupted by said object, and decision means responsive to an output from said determining means and to stored data for determining said characteristic of said object.

19. A device according to claim 18, wherein said characteristic is the dimension of said object in a direction parallel to said one direction.

* * * * *